United States Patent
Dillen

(10) Patent No.: US 9,743,913 B2
(45) Date of Patent: Aug. 29, 2017

(54) UNOBTRUSIVE OVULATION TRACKING SYSTEM AND METHOD USING A SUBJECT'S HEART RATE

(71) Applicant: KONINKLIJKE PHILIPS N.V., Eindhoven (NL)

(72) Inventor: Paulus Henricus Antonius Dillen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/112,267

(22) PCT Filed: Mar. 31, 2015

(86) PCT No.: PCT/EP2015/057136
§ 371 (c)(1),
(2) Date: Jul. 18, 2016

(87) PCT Pub. No.: WO2015/150434
PCT Pub. Date: Oct. 8, 2015

(65) Prior Publication Data
US 2017/0007214 A1     Jan. 12, 2017

(30) Foreign Application Priority Data

Apr. 1, 2014   (EP) .................................. 14163069

(51) Int. Cl.
*A61B 5/02*     (2006.01)
*A61B 10/00*    (2006.01)
(Continued)

(52) U.S. Cl.
CPC ........ *A61B 10/0012* (2013.01); *A61B 5/0002* (2013.01); *A61B 5/02055* (2013.01);
(Continued)

(58) Field of Classification Search
CPC ........................... A61B 10/00; A61B 5/02405
See application file for complete search history.

(56) References Cited

U.S. PATENT DOCUMENTS

2008/0114219 A1* 5/2008 Zhang ................ A61B 5/02055
                                                600/301
2009/0189746 A1   7/2009 Ullrich
(Continued)

FOREIGN PATENT DOCUMENTS

CN      102871691 A     1/2013
EP        0132119 A2    1/1985
(Continued)

OTHER PUBLICATIONS

Razon, S. et al., "The Effect of Olfactory Ovulation Cues on Males' Attention Allocation and Perception of Exertion", Itay Basevitch, Florida State University, DigiNole Commons, Educational Psychology and Learning Systems, Jul. 1, 2013 http://diginole.lib.fsu.edu/edpsy_faculty_publications.
(Continued)

*Primary Examiner* — Christopher D Koharski
*Assistant Examiner* — Natasha Patel
(74) *Attorney, Agent, or Firm* — Sherry Austin

(57) ABSTRACT

The present invention relates to a system for unobtrusive fertility tracking, comprising a sensor for obtaining a heart signal, a processing unit configured to determine a subject's heart rate from the heart signal, and an evaluation unit configured to analyze the subject's heart rate to predict likelihood of ovulation. The processing unit is further configured to extract heart rate variability features from the heart signal, and the evaluation unit is further configured to predict likelihood of ovulation based on the heart rate variability features.

20 Claims, 5 Drawing Sheets

(51) Int. Cl.
*A61B 5/024* (2006.01)
*A61B 5/11* (2006.01)
*A61B 5/00* (2006.01)
*A61B 5/0205* (2006.01)
*A61B 5/01* (2006.01)

(52) U.S. Cl.
CPC ...... *A61B 5/02405* (2013.01); *A61B 5/02416* (2013.01); *A61B 5/02438* (2013.01); *A61B 5/1118* (2013.01); *A61B 5/1128* (2013.01); *A61B 5/681* (2013.01); *A61B 5/01* (2013.01); *A61B 2010/0019* (2013.01); *A61B 2010/0029* (2013.01); *A61B 2560/0252* (2013.01)

(56) References Cited

U.S. PATENT DOCUMENTS

| | | | |
|---|---|---|---|
| 2010/0174153 | A1 | 7/2010 | Nakagawa |
| 2012/0179012 | A1 | 7/2012 | Saffarian |
| 2012/0289842 | A1 | 11/2012 | Gutman |
| 2016/0015314 | A1* | 1/2016 | Dusanter .............. A61B 5/4812 600/301 |
| 2016/0058429 | A1* | 3/2016 | Shinar ................ A61B 10/0012 600/551 |

FOREIGN PATENT DOCUMENTS

| | | |
|---|---|---|
| GB | 2437250 A | 10/2007 |
| JP | 1184036 A | 3/1999 |
| JP | 200694969 A | 4/2006 |
| JP | WO2013171799 A1 | 1/2016 |
| WO | WO2005020841 A2 | 3/2005 |
| WO | WO2013043747 A1 | 3/2013 |
| WO | WO2013171799 A1 | 11/2013 |
| WO | WO2014002276 A1 | 1/2014 |

OTHER PUBLICATIONS

DMcKay, M. et al. "Vitality Band and Diagnostic Tool", Dr Hari Kalva Electrical Engineering, pp. 1-20, Apr. 16, 2013.

Leicht, Anthony S. et al., "Heart Rate Variability and Endogenous Sex Hormones During the Menstrual Cycle in Young Women", Experimental Physiology: Translation and Integration, May 2003; vol. 88, No. 3, pp. 441-446. http://www.ncbi.nlm.nih.gov/m/pubmed/12719769.

"Monitoring Your Fertility", 2016 fertilityfactor, pp. 1-5 http://www.fertilityfactor.com/infertility_trying_to_conceive_monitors.html.

Nakamura M. et al., "Changes in Cardiac Autonomic Nervous Activity During Menstrual Cycle of Young Women", Japanese Journal of Physical Fitness and Sports Medicine, vol. 51, 2002, pp. 307-316.

Matsumoto K. et al., "The Effects of Bright Light Therapy on Auto-nomic Nervous Activities during Menstrual Cycle", Yamaguchi Medical Journal, vol. 55, No. 5, pp. 167-172, 2006.

* cited by examiner

UNOBTRUSIVE OVULATION TRACKING SYSTEM AND METHOD USING A SUBJECT'S HEART RATE

CROSS-REFERENCE TO RELATED APPLICATIONS

This application is the U.S. National Phase application under 35 U.S.C. §371 of International Application No. PCT/EP2015/057136, filed on Mar. 31, 2015, which claims the benefit of European Patent Application No. EP14163069.9, filed on Apr. 1, 2014. These applications are hereby incorporated by reference herein.

FIELD OF THE INVENTION

The present invention relates to a system and a corresponding method to unobtrusively track and predict the fertile periods of a subject analyzing the subject's heart rate.

BACKGROUND OF THE INVENTION

Many adults develop the wish to have children. However, it is commonly known that becoming pregnant can be a non-trivial objective. Depending on a variety of factors, it may be hard (or ultimately impossible) to even start the pregnancy. One of those factors is the precise moment of conception. It is only during the most fertile days of the menstrual cycle that the optimal conditions for getting pregnant are satisfied.

The woman's fertility varies throughout her monthly cycle, and actually, conception can only occur shortly (within 12 hours) after the ovulation. The ovum released during ovulation only has a lifetime of up to 48 hours and the sperm survives in the vaginal environment for an average of 60 to 120 hours. During the fertile period, the vaginal environment becomes more welcoming and friendly to sperm. Cervical mucus becomes less acidic and more elastic and the cervix moves from a low, firm, dry and closed position to being soft, high and open. All these changes facilitate the passage of sperm to the uterus and the Fallopian tubes, where fertilization of the released ovum usually occurs.

Because the day of ovulation is important to understanding fertility, many women tend to monitor their bodies for signs of ovulation. However, although many women think they know when they ovulate, it is quite likely that not a lot do actually know. Hence, several tests and tools have been developed and are commercially available to assist in predicting the fertile period.

Basal (or Core) Body Temperature (BBT) Thermometers are used to measure the core body temperature at certain times of the day. When women ovulate, their core temperature rises by half a degree to a full degree because of the extra progesterone in their body. Although the temperature can fluctuate throughout the month, a sustained increase in body temperature is indicative of the ovulation having occurred. With BBT thermometers, the temperature is tracked during the monthly period, typically by a daily oral measurement protocol, and the periodic nature of the woman's cycle can be used to predict the fertile period after a few months of measurements.

A similar approach is applied by Luteinizing Hormone (LH) Testing Kits which measure the LH levels in the woman's urine. Luteinizing hormone LH is produced by gonadotroph cells in the anterior pituitary gland. An acute rise of LH triggers ovulation. LH Testing Kits are available in the form of dipsticks which change color if ovulation will happen within 24 to 48 hours. The fertility tracking using these kits is similar to BBT thermometers and requires a strict protocol since the LH levels have to be measured at the same time every day.

The aforementioned methods are usually combined with electronic monitoring devices which assist a person to follow the protocol. These monitoring devices usually keep track of the measurements and indicate when another measurement is required. Furthermore, by tracking the measurements of several methods and combining these with the periodic nature of the menstrual cycle, the monitoring devices are capable of predicting the fertile periods very precisely.

The monitoring devices assist in following the protocol but will not replace it. Hence, the fairly small but non-negligible burden of explicit protocol remains. Its daily nature, combined with the short fertile time window, means that no days shall be skipped, and in many cases, this protocol has to be sustained for months in a row. Especially, the strict timing of BBT and LH measurements can be hampering in real-life settings, and a deviation may reduce the reliability of the outcome. Furthermore, to be forced to take measurements at a certain time slot can pose privacy issues, as one is not always under control of the social setting at a given moment of the day. Hence, there is a need for an improved device and method.

JP 2006-094969 discloses a method and an apparatus for determining female menstrual cycles by measuring continuously a heart rate of a subject. The menstrual cycle and ovulation dates are estimated by comparing the day average value with the monthly average value of the heart rate.

SUMMARY OF THE INVENTION

It is an object of the present invention to provide an alternative system for determining the fertile periods of a subject that is less complex, unobtrusive and is more reliable. Furthermore, a corresponding method shall be provided.

In a first aspect of the present invention a system for unobtrusive ovulation tracking is presented, comprising:
  a sensor for obtaining a heart signal,
  a processing unit configured to process the heart signal, and
  an evaluation unit configured to analyze the heart signal to predict likelihood of ovulation,
wherein the processing unit is configured to extract heart rate variability features from the heart signal, and wherein the evaluation unit is further configured to predict likelihood of ovulation based on the heart rate variability features.

In a further aspect of the present invention a method for unobtrusive ovulation tracking is presented, comprising:
  obtaining a heart signal from a sensor,
  processing the heart signal,
  analyzing the heart signal to predict likelihood of ovulation
wherein the method further comprises the steps of:
  extracting heart rate variability features from the heart signal, and
  predicting likelihood of ovulation based on the heart rate variability features.

In yet further aspects of the present invention, there are provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Several embodiments of the invention are defined in the dependent claims. It shall be understood that the claimed methods, processor, computer program and medium have similar and/or identical embodiments as the claimed system and as defined in the dependent claims.

It is thus an idea of the present invention to predict ovulation based on a subject's heart signal. Thereto, the proposed system comprises a sensor to obtain a heart signal from the subject, and a processing unit to determine indicative features from said signal. The heart signal can be for instance a photoplethysmography (PPG) signal, an electro cardiogram (ECG) signal, or a combination of both. From the heart signal an evaluation unit assesses the likelihood of ovulation.

The proposed system thus uses an indicator for determining the fertility time window of a female that can be assessed unobtrusively.

An unobtrusive measurement has the advantage that it is generally more easily to be applied, and is therefore frequently more accepted. It may be smoothly integrated into the daily routine and may consequently reduce deviations from the strict measurement protocol. Furthermore, besides the simplicity, an unobtrusive measurement is usually more comfortable.

Using a heart signal as an indicator has the further advantage that the measurement process may be performed automatically. Automating the process has several advantages over conventional manual assessment.

The measurement may be initiated by the system at regular intervals. Thus, a strict protocol may be followed without manual intervention. The automated measurement can ensure that no measurements are forgotten, and the strict protocol may be sustained easily over a period of several months. The longer a precise schedule is maintained the better and more reliable becomes the prediction of the menstrual phases and ovulation.

Moreover, obtaining a heart signal is not limited to specific sensors. Several sensors are available that can produce a robust heart signal. Many of these sensors are already available in devices of our daily life, and may thus be reused in conjunction with the proposed system. This way, the proposed system may replace special sensors or testing kits and thus proposes a cost saving alternative.

Overall, the proposed system allows for a simple and comfortable determination of the fertility time window of a female and at the same time enhances the reliability of long term assessments.

Finally, since the heart rate variability features correlate with estrogen levels during ovulation, they are used to predict the likelihood of ovulation. Hence, the prediction becomes more accurate and reliable.

According to an embodiment of the system, the evaluation unit comprises a phased locked loop which locks onto the heart rate variability features to predict likelihood of ovulation. The use of a phased locked loop makes it possible to adapt to fluctuations in the heart rate variability pattern. As a consequence, this enables a more accurate forecast than the prior art system, which is based instead on a mere averaging of heart rate data over a monthly period, the prior art system being in fact more able to perform detection of ovulation dates than to achieve a real prediction of said ovulation dates.

According to a further embodiment of the system, the proposed system comprises an activity determination unit configured to provide an activity indicator indicative of a current activity level and/or a user's physical condition, in particular a circadian rhythm or phase of the subject, wherein the evaluation unit is further configured to predict the likelihood of ovulation based on said activity indicator. By determining the current activity level the system can be further automated. It allows measuring the heart rate at an appropriate time, for instance, while the subject is relaxed but awake, in a neutrally temperate environment, and not having recently exerted herself.

According to a further embodiment of the system the proposed system comprises a motion sensor configured to determine motion and/or orientation data of the subject, wherein the activity determination unit is configured to provide the activity indicator based on said motion and/or orientation data. The reliability of the activity indicator is advantageously enhanced by the motion and/or orientation data, since it can indicate if a person is currently at rest or active. This way, more reliable measurements are feasible.

According to a further embodiment of the system the proposed system comprises an ambient sensor configured to determine an ambient temperature and/or ambient light levels, wherein the activity determination unit is configured to provide the activity indicator based on said ambient temperature and/or ambient light levels. The ambient temperature and/or ambient light levels contribute in the assessment of a viable activity indicator and thus further facilitate an autonomous measurement.

According to a further embodiment of the system the proposed system comprises a calendar unit configured to track local date and time information, wherein the activity determination unit is configured to provide the activity indicator based on said local date and time information. Advantageously, the date and time information is used to determine the circadian rhythm of a subject. In chronobiology the circadian rhythm is the endogenous, biological process that displays an oscillation of about 24 hours. Advantageously, the circadian rhythm of a subject is taken into account while assessing the activity indicator. There are indications that the period of ovulation is also related to the circadian rhythm or phase.

Advantageously, the previous mentioned embodiments related to the activity indicator are combined to obtain a precise activity indicator. For instance, night-time conditions can be inferred from little to no motion, horizontal orientation, low light level and a constant ambient temperature in a certain personal range. Combined with the local time, a fair assessment can be made, whether a person is asleep and hence in a suitable condition for the measurement of a resting heart signal.

According to a further embodiment of the system the proposed system comprises a data storage for archiving the subject's heart signal and/or other sensor data, wherein the evaluation unit is further configured to predict the likelihood of ovulation based on subject's current and archived heart signal and/or the other sensor data. This way, the heart signal can easily be analyzed over time by comparing the heart signal of different periods. Advantageously, the data is maintained for several months to allow a viable prognosis of future ovulations. The other sensor data can include any sensor data not related to the subject's heart signal that may assist in the assessment.

According to a further embodiment of the system the proposed system comprises a communication unit for wirelessly exchanging data with external sensors and/or processing units and/or user input, wherein the evaluation unit is further configured to predict the likelihood of ovulation based on said data. This way, the multiple components can communicate with each other wirelessly. The sensors can thus be at a position for optimal measurements, whereas the processing is done centralized, for instance by the processing unit available in a smartphone. Additionally, the system can obtain input from other sensors such as data of the core temperature of a subject to further refine the assessment. Hence, the system is more flexible and scalable.

According to a further embodiment of the system the proposed system comprises a data integration unit configured to integrate testing results from other fertility tracking devices, in particular luteinizing hormone testing devices and/or basal body temperature thermometers, wherein the evaluation unit is further configured to predict the likelihood of ovulation based on the heart signal and/or the testing results from other fertility tracking devices. Advantageously, the assessment based on the heart signal is refined using the results of other fertility tracking devices. Advantageously, these devices provide the assessment in electronic format such that the evaluation unit can directly consider these results while assessing the likelihood of ovulation based on the heart signal. However, it is also conceivable that such results are provided manually to the system, for instance as training data, to adjust the system to particular user requirements.

According to a further embodiment of the system the proposed system comprises a training unit configured to adjust the evaluation unit based on training data and/or individual user input. This way, self-learning can be implemented using training sets such as statistics gathered from a given population or external ground truths provided by the user, for instance, start and end dates of the last menstruation. The system is thus customizable and adaptable to the specific user requirements.

According to a further embodiment the sensor is an optical heart rate sensor. Thus, the heart signal is obtained with a sensor that can be widely applied on various parts of the subject's body, compared to other electrocardiographs that restrict the sensing location to e.g. the chest. Hence, optical heart rate sensors such as photoplethysmography (PPG) sensors are in particular suited for unobtrusive measurements.

According to a further embodiment the sensor is a body-worn sensor. Body-worn means that the sensor can be integrated into cloths or accessories the subject is regularly wearing. Advantageously, the sensor can be integrated into accessories such as a watches, wristbands or necklaces allowing for a comfortable, yet continuous, measurement of the subject's heart rate.

According to an alternative embodiment the sensor is detached from the subject, in particular a camera and/or a biofeedback device. Thus, in this alternative the sensor is not in direct contact with the subject. For instance, a heart signal can be obtained from analyzing images of the subject taken by one or more cameras. Cameras can be found in many devices of the daily life, in particular, devices connected to a network such as PCs, laptops or smartphones. Appropriate footage can thus be obtained from already existing sensors and analyzed by a central processing unit. Where a single heart rate measurement of such a device might not always yield a precise result, an average over multiple measurements may be suitable for an overall assessment, in particular, if the system provides self-learning capabilities.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
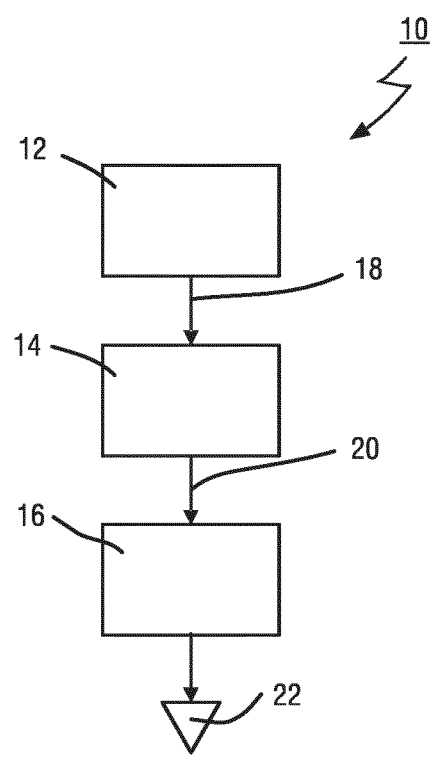
FIG. 1 shows an embodiment of a system according to the present invention.

FIG. 1 shows a first embodiment of the system according to the present invention. The system is denoted in its entirety with reference numeral 10. The proposed system comprises a sensor 12, a processing unit 14 and an evaluation unit 16.

The sensor 12 may be any device configured to obtain a heart signal 18 from a subject. In one embodiment the sensor 12 could be an electrocardiograph (ECG) with electrodes placed on the subject's skin. ECG is used to measure the heart's electrical conduction system. It picks up electrical impulses generated by the polarization and depolarization of cardiac tissue and translates into a waveform (heart signal). The waveform is then used to measure the rate and regularity of heartbeats.

In an embodiment, the sensors are photoplethysmographs (PPG). Photoplethysmography is an optical measurement technique that evaluates a time-variant change of light reflectance or transmission of an area or volume of interest. PPG is based on the principle that blood absorbs light more than surrounding tissue, so variations in blood volume with every heartbeat affect transmission or reflectance correspondingly. A distinction is made between contact PPG sensors and non-contact, remote PPG (rPPG) sensors.

Contact PPG devices measure the heart rate and sometimes also the (arterial) blood oxygen saturation (also called SpO2) of a subject using sensors attached to the skin of the subject, for instance to a fingertip, earlobe or forehead.

Non-contact, remote PPG (rPPG) devices are based on the same principal as contact PPG devices, but utilize light sources or, in general radiation sources, disposed remotely from the subject of interest. Similarly, also a detector, e.g., a camera or a photo detector, can be disposed remotely from the subject of interest. Therefore, remote photoplethysmographic systems and devices are considered unobtrusive and are well suited for medical as well as non-medical everyday applications.

It shall be noted that the invention is not limited to any of these sensors. Other sensors such as a seismocardiograph, or even a combination of several different sensors are conceivable as well.

The heart signal 18 obtained by the sensor 12 is processed by a processing unit 14. In an embodiment, the heart signal 18 is provided as a continuous data stream. The processing unit 14 could be a microcontroller such as an ASIC, DSP or a FPGA which is specifically designed for this task. In other embodiments the processing unit could be part of a general purpose processing unit, for instance that of a PC or smartphone. The processing unit processes the heart signal and advantageously extracts multiple indicators such as the subject's heart rate 20, heart rate variability features, or a combination of both. An indicator could for instance be the short-term averaged heart rate 20.

The evaluation unit 16 predicts the likelihood of ovulation 22 based on said indicator, e.g. the heart rate 20. Advantageously, the assessment is an analysis of the heart rate 20 over time. During ovulation the resting heart rate is significantly higher than during other times of the menstrual cycle. Therefore, the evaluation unit 16 is configured to detect periods of higher heart rate. Advantageously, the evaluation unit 16 compares daily heart rate values with previous measurements taken under similar conditions to detect an absolute change in heart rate 20.

Based on the assessment the evaluation unit 16 may provide the likelihood of ovulation 22 on a defined scale or as percentage value. In other embodiments the evaluation unit 16 might indicate periods of high likelihood of ovulation 22 by a simple alarm. The evaluation unit 16 could be a microcontroller similar to the processing unit 14. In other embodiments the processing unit 14 and the evaluation unit 16 may be combined into a single device. The evaluation unit 16 is, however, not limited to any specific device. It is also conceivable that the evaluation is performed by specialized data processing means, for instance by a dedicated processor or by data mining using dedicated software. In such a case the heart rate data could be stored in a database with special algorithms for determining variations of the heart rate over time.

Figure 2:
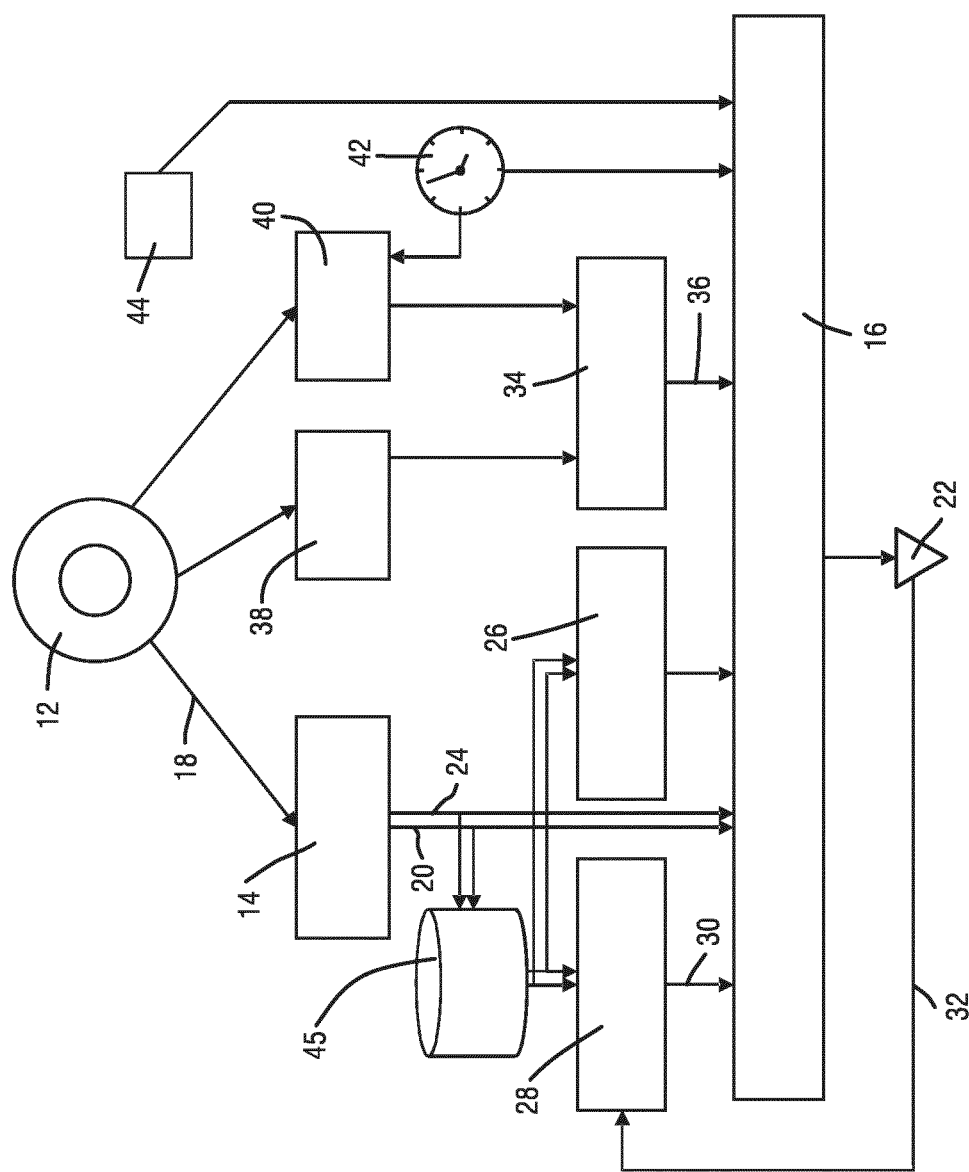
FIG. 2 shows a schematic diagram of an embodiment of a system according to the present invention.

FIG. 2 shows in detail an embodiment of the present invention. According to this embodiment, the sensor 12 is a multi-sensor unit which provides inter alia a heart signal 18. The heart signal 18 is here an inter-beat interval (IBI) signal representing the time interval between individual beats of the heart. In normal heart function IBI values vary from beat to beat. This natural variation is known as heart rate variability (HRV). In this embodiment the processing unit 14 is configured to determine the heart rate 20 and the heart rate variability 24 from the heart signal 18.

The heart rate variability 24 is a physiological phenomenon of variation in the time interval between heart beats. It relates to a variety of psychological life pattern factors (stress, attention, etc.) and physical (body strain, eating, ambient temperature) factors. Inter alia there is a correlation between HRV and estrogen levels. In particular, it has been shown that there is a significant correlation between absolute measures of HRV and 17β-oestradiol at ovulation. HRV may, hence, be a further indicator for ovulation. "Absolute" means in this context that there is a rise in all HRV components (low frequency LF, high frequency HF and total power TP) of the HRV power spectrum. The components may be determined by fast Fourier transformation (FFT) of the HRV signal. The correlation between ovulation and HRV is explained in further detail with reference to FIG. 5.

The HR and HRV values are fed into the evaluation unit 16. The evaluation unit 16 is in this embodiment configured to processes data from several data source. Hence, the evaluation unit 16 works as a data integration unit combining the data from several inputs to determine the likelihood of ovulation 22.

Accordingly, further input may be provided by a statistical unit 26 which provides statistical input related to HR and HRV. Advantageously, the statistical unit provides statistics about the distribution of HR and HRV over time. However, the statistical unit is not limited to an assessment over time. It may further include any collection, organization, analysis, interpretation and presentation of the HR and HRV data which may lead to a refined assessment of the likelihood of ovulation 22. The output of the statistical unit is fed into the evaluation unit 16.

Further input to the evaluation unit 16 may be provided by a menstrual phase determination unit 28. Such a unit is configured to provide a menstrual phase indicator 30 indicative of the current phase of the menstrual cycle. The menstrual phase determination unit 28 takes HR and HRV values as input and is configured to predict the current phase of the menstrual cycle based upon these values. The determination unit 28 preferably comprises a Phased Locked Loop PLL which locks onto HR and/or HRV data collected by the statistical unit 26 to give a running forecast. This PLL adapts to fluctuations in the HR/HRV patterns. It enables a more accurate forecast than by summing up a monthly period.

Due to the periodic nature of the menstrual cycle, the menstrual phase determination unit 28 further takes the predicted ovulation time 22—thus the output of the evaluation unit 16—as input to align its assessment with the results of the evaluation unit 16. Thus, the menstrual phase determination unit 28 acts together with the evaluation unit 16 and the feedback loop 32 as a closed loop. Accordingly, the menstrual phase determination unit 28 is similar to a phase detector of a phase-locked loop (PLL).

Further input to the evaluation unit 16 may be provided by an activity determination unit 34. The activity determination unit 34 is configured to provide an activity indicator 36 indicative of the current activity level of the subject and/or the user's physical condition. Such indicator is in particular advantageous for determining the appropriate time for a HR/HRV measurement. The relevant basal or resting heart rate, which is of main interest, is measured while the subject is relaxed but awake, in a neutrally temperate environment, and not having recently exerted herself nor having been subject to a stress or even a surprise. Such conditions may be determined by the activity determination unit 34 based on inputs from a variety of sources.

According to the embodiment shown in FIG. 2 input for the activity determination unit 34 may be obtained from a motion sensor 38. The motion sensor 38 may provide acceleration and/or 3D-orientation data. From the acceleration and/or 3D-orientation data inertial features may be computed which indicate whether a person is at rest or active. Such data is processed by the activity determination unit 34 to provide an indicator in which state the subject is at the moment. Said activity indicator 36 is fed into the evaluation unit 16 and considered for the assessment, in particular, for determining the appropriate time window for the assessment.

Additionally, the proposed system comprises in this embodiment an ambient sensor 40 for determining the surrounding conditions, for instance, the ambient temperature and/or ambient light levels. The ambient temperature and/or ambient light level data are also processed by the activity determination unit 34 to provide further indications regarding the current state of the subject.

It shall be noted that the motion sensor 38 and the ambient sensor 40 are only examples of input feeds to the determination unit 34. The activity determination unit 34 may also process further data which may be indicative of the current state or the health level of the subject.

The proposed system may further include a calendar unit 42 indicated here by a clock symbol. The calendar unit 42 is configured to track local date and time information. Such data may be fed into the activity determination unit 34 or directly into the evaluation unit 16.

For the activity determination unit 34, time and date information is a relevant factor in determining the current state of the person. For instance, it can be assumed that a person is usually more likely at rest during night time than at day time. Advantageously, the activity determination unit 34 determines the subject's personal circadian rhythm.

The evaluation unit 16 may further directly process the date and time information for scheduling the measurements and the assessment of the provided input data. In particular, the periodic nature may be taken into account based on the time and information data provided by the calendar unit 42. For instance, in combination with the activity indicator 36 the time and date data may be used to determine a suitable point during the day at which a measurement may be taken. This way, the system may automatically adapt to the needs of the subject by means of self-learning.

Self learning may be addressed by a further training unit 44 configured to train and adjust the evaluation unit 16. Generally, a set of training data gathered from multiple individuals is used as a baseline to initialize the evaluation unit 16. Furthermore, manual data collected by the individual user may be used as input. In an embodiment, the evaluation unit 16 may be trained continuously during use. For instance, the subject could provide external ground truth to which the systems adapts, such as start and end of menstruation. The training unit 44 thus allows for customization and an individual configuration of the system. Given the nature that the menstrual cycle varies for each woman, the training unit 44 may significantly enhance the reliability of the system.

All data that is fed into the evaluation unit can be archived in a data storage 45 for reuse in a later assessment. In FIG. 2 only HR and HRV data is archived. The data storage 45 is, however, not limited to these particular values.

Figure 3:
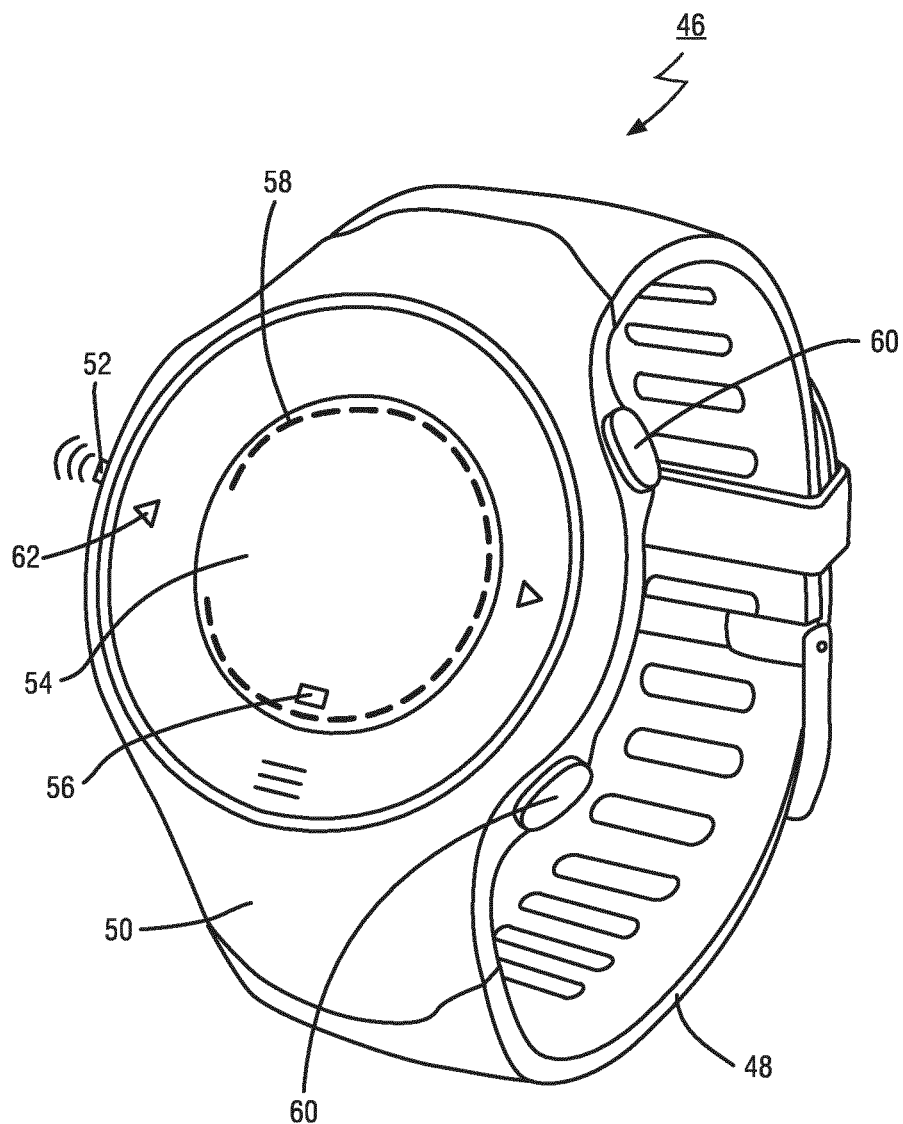
FIG. 3 shows a further embodiment of the present invention, FIG. 4 show an alternative embodiment of the present invention.

FIG. 3 shows an embodiment of the proposed system. According to this embodiment the proposed system is integrated as a single device into a wristwatch 46. The wristwatch 46 is similar to a normal watch and can be worn on a daily basis. The wristwatch 46 comprises a wristband 48 and a watch unit 50. Advantageously, the watch unit 50 comprises one or more microprocessors configured to function as processing and evaluation units. The wristwatch 46 comprises at least one sensor unit for obtaining a heart signal of the person wearing the watch.

In an embodiment, the sensor is integrated into the watch unit 50, for instance as an optical heart rate sensor such as a PPG or rPPG sensor. Such a sensor comprises light-emitting diodes on the backside of the watch unit 50 facing the subject's skin. The light-emitting diodes emit light of a certain type onto the skin in a pulsating manner. A further electro-optical cell senses the reflected light and determines the volume of blood under the skin as explained in details with reference to FIG. 1. The obtained heart signal may be further processed by the processing unit to detect the subject's true heart rhythm. It shall be noted that the system is not limited to such a PPG sensor. In other embodiments alternative sensors, for instance an ECG sensor in the form of a chest strap may be used. Such chest straps may comprise conductive smart fabric with built-in microprocessors which analyze the heart signal to determine the true heart rate. The heart signal and/or the true heart rate are subsequently transmitted, advantageously wirelessly, to the wristwatch 46.

The wristwatch 46 may further comprise additional sensors such as motion and ambient sensors, determining additional parameters which may be processed to enhance the assessment by the evaluation unit. Yet in another embodiment the wristwatch 46 comprises a communication unit 52 for exchanging data with external devices. External devices could be additional sensors and/or processing units and/or storage devices. The communication may use conventional standards such as Bluetooth.

The wristwatch 46 may further include a display 54 for displaying current system information, in particular, an indicator of the likelihood of ovulation. Additionally, the display 54 may present standard data such as time and date. In an embodiment the wristwatch 46 functions as a normal watch with an alarm function notifying the user if the likelihood of ovulation has reached a certain threshold. The likelihood of ovulation may be presented as a percentage indicator or as a simple Yes/No indicator 56. The display 54 may further present the current menstrual phase indicated here with the ring-shaped progress bar 58.

It shall be noted that the proposed system is not limited to an integrated display 54. Other embodiments may comprise external displaying means for notifying the user. For instance, progress could be tracked on an external computer system and the current state may be visualized on that system. It is also conceivable that other notifying means are used such as e-mail or instant messaging.

In an embodiment, the wristwatch 46 further comprises input means such as dedicated buttons for interacting with the system. The input means are indicated here by two input buttons 60 on the side of the watch unit 50 and navigational input buttons 62 next to the display 54. Besides general input for controlling the system or navigating through a menu, the input means 60, 62 may be used in an embodiment to provide user-specific input to train the evaluation unit and to adapt it to the individual user requirements. In other embodiments, the input may be provided by external devices, for instance a smartphone, so that no input means at the wristwatch 46 are required.

Figure 4:
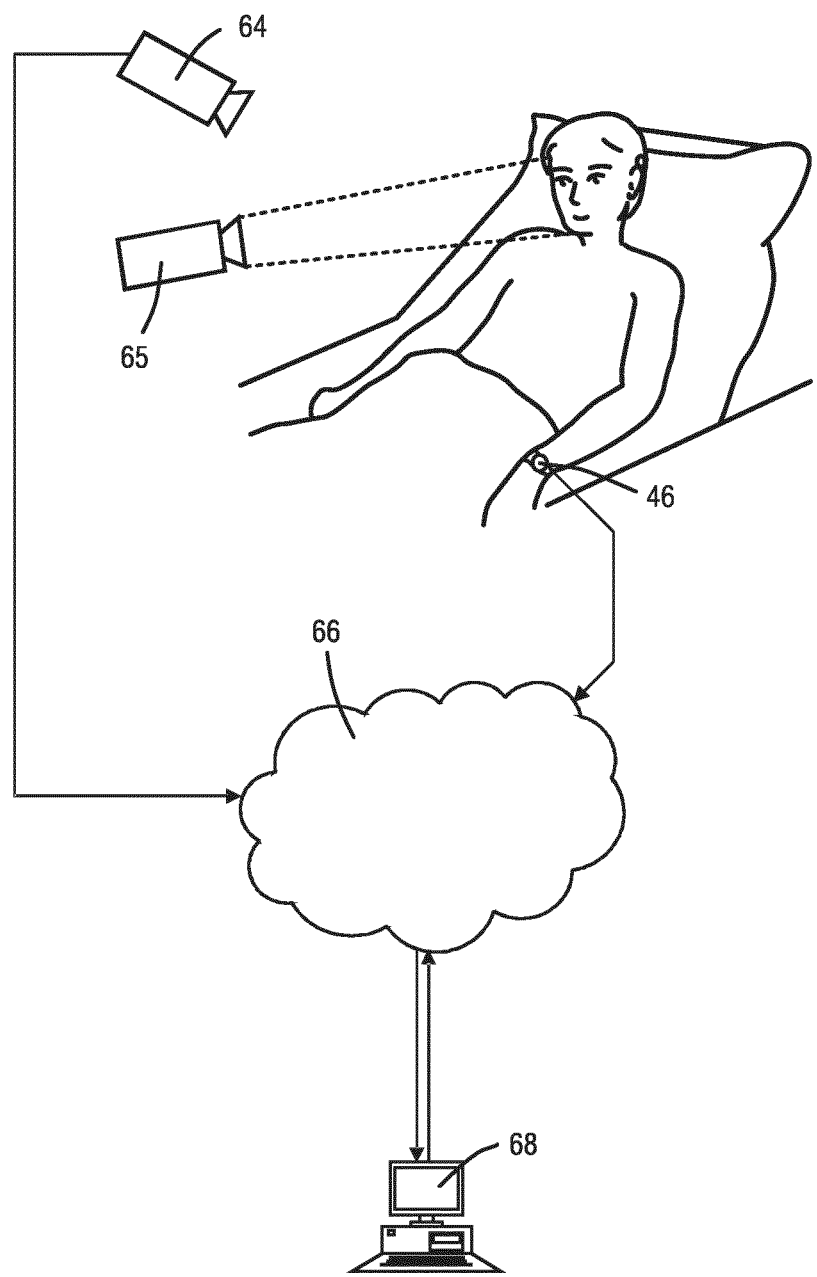

As mentioned before, the system is not limited to a monolithic device as depicted in FIG. 3. With reference to FIG. 4, a system according to the present invention is shown with distributed components.

Such a system may comprise one or more sensors that provide heart signals of a subject. The sensors may include a wristwatch 46 as shown in FIG. 3 and/or remote PPG sensors as indicated here by the camera device 64 and the optional dedicated light source 65. The camera device 64 could be a simple digital, consumer level photo camera as they are available in smartphones, PCs or surveillance cameras. Such a camera usually includes a photosensor, such as a CMOS or CCD sensor, which may also operate in a specific spectral range (visible, IR) or provide information for different spectral ranges. The camera may provide an analog or digital signal.

The light source 65 could be a simple lamp for illuminating regions of interest, such as the skin of the subject's face, with light in a first wavelength range to obtain reflected light from said region of interest which is detected by the camera device 64. In another embodiment no dedicated light source is provided, but ambient light is used for illumination of the subject in the reflective mode. From the reflective light only light in the desired wavelength range (e.g. green light) is detected and/or evaluated.

The camera device 64 forwards recorded image frames to a central unit 66 of the system. The central unit 66 is depicted here as cloud and comprise besides the aforementioned processing unit and evaluation unit, in particular image processing means to extract a PPG signal (heart signal) from the image data. As described above, from the PPG signal the heart rate of the subject is determined and processed in the aforementioned manner to obtain the likelihood of ovulation.

The subject is here depicted lying in bed and being at rest. Other settings are conceivable as well, e.g. the subject being at work sitting in front of a computer, wherein the camera device 64 is an integrated camera in the computer screen. Any setting in which suitable footage of the subject can be obtained may be used in the assessment. Advantageously, several data feeds are combined for the final assessment.

Hence, the central unit 66 may further act as data integration unit collecting, storing and assessing further data from other data sources or archives to enhance the prediction.

Interacting with the cloud could be implemented as web interface as depicted here by the computer 68. Via the web interface 68 the user can provide additional data, for instance, obtained from other fertility tracking means such as basal body temperature thermometers or luteinizing hormone testing kits. Furthermore, the central unit 66 may inform the user over the current state and the likelihood of ovulation using the web interface 68. Advantageously, the web interface 68 provides a central information system for the overall fertility tracking. Alternatively, the output is transferred back to the sensor, for instance, to the wristwatch 46.

With reference to FIGS. 3 and 4, a fully integrated system (FIG. 3) and a distributed system (FIG. 4) are shown as embodiments of the proposed system. It shall be noted that further embodiments are conceivable that are partially integrated and partially distributed. Hence, the proposed system is scalable from an integrated to a distributed system without leaving the scope of the present invention.

Figure 5:
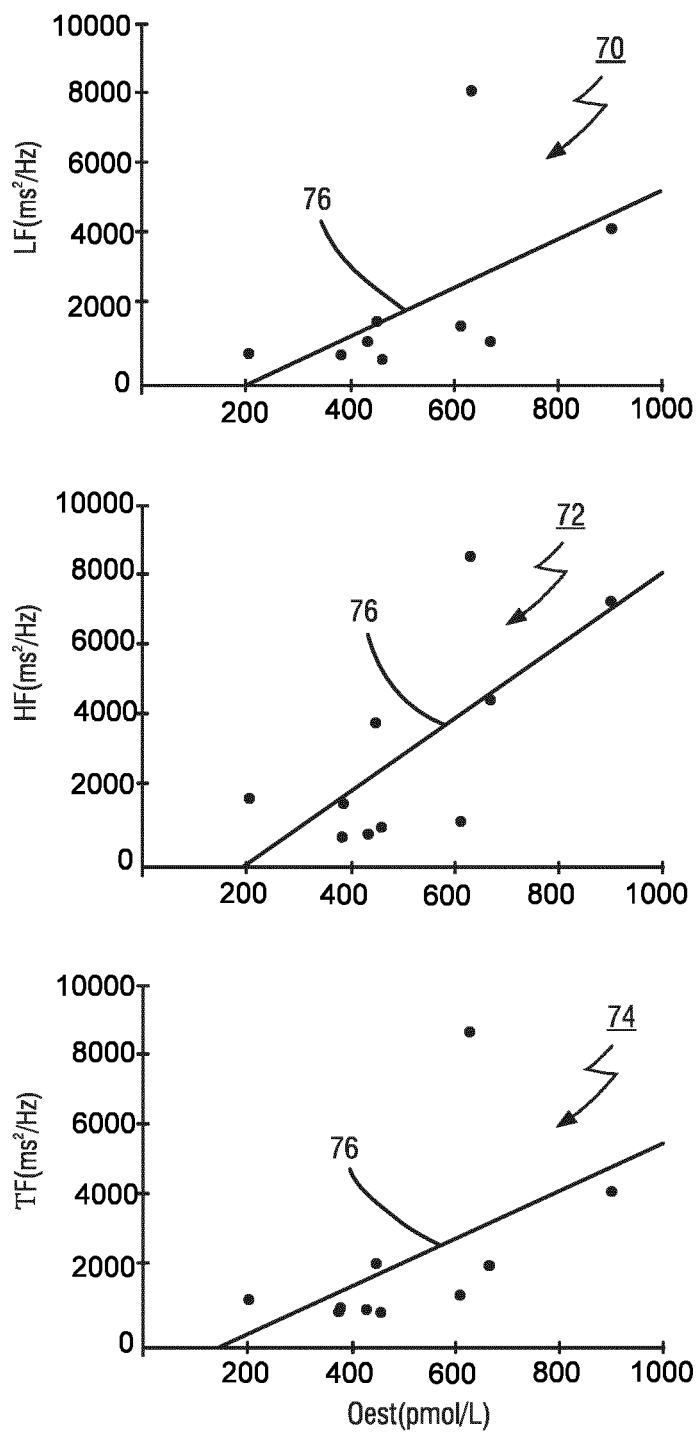
FIG. 5 shows sample training data for an embodiment of the present invention.

FIG. 5 shows as an example of HRV recordings of ten individuals, in particular, the low frequency (LF, 0.041-015 Hz) 70, the high frequency (HF, 015-0.8 Hz) 72 and the total power (TP, 0-0.1 Hz) 74 component of the power spectrum. Depicted is the correlation between the heart rate variability and the estrogen (17β-oestradiol) levels of the individuals. As indicated by the linear regression lines 76 an increased estrogen level leads to an absolute rise in all HRV components. This relation may be utilized as one indicator to determine the likelihood of ovulation as described by the various embodiments.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A system for unobtrusive ovulation tracking, comprising:
   a sensor for obtaining a heart signal;
   a processing unit configured to process the heart signal; and
   an evaluation unit configured to analyze the heart signal to predict likelihood of ovulation, wherein the processing unit is configured to extract heart rate variability features from the heart signal, and wherein the evaluation unit is further configured to predict likelihood of ovulation by correlating absolute measures of the heart rate variability features to estrogen levels.

2. The system according to claim 1, wherein the evaluation unit comprises a phased locked loop which locks onto the heart rate variability features to predict likelihood of ovulation.

3. The system according to claim 1, further comprising an activity determination unit configured to provide an activity indicator indicative of a current activity level and/or a user's physical condition, in particular a circadian rhythm or phase of the subject, wherein the evaluation unit is further configured to predict the likelihood of ovulation based on said activity indicator.

4. The system according to claim 3, further comprising a motion sensor configured to determine motion and/or orientation data of the subject, wherein the activity determination unit is configured to provide the activity indicator based on said motion and/or orientation data.

5. The system according to claim 3, further comprising an ambient sensor configured to determine an ambient temperature and/or ambient light levels, wherein the activity determination unit is configured to provide the activity indicator based on said ambient temperature and/or ambient light levels.

6. The system according to claim 3, further comprising a calendar unit configured to track local date and time information, wherein the activity determination unit is configured to provide the activity indicator based on said local date and time information.

7. The system according to claim 1, further comprising a data integration unit configured to integrate testing results from other fertility tracking devices, in particular luteinizing hormone testing devices and/or basal body temperature thermometers, wherein the evaluation unit is further configured to predict the likelihood of ovulation based on the heart signal and/or the testing results from other fertility tracking devices.

8. The system according to claim 1, further comprising a data storage for archiving the heart signal, wherein the evaluation unit is further configured to predict the likelihood of ovulation based on a current and an archived heart signal.

9. The system according to claim 1, further comprising a communication unit for exchanging data with external sensors and/or processing units and/or user input, wherein the evaluation unit is further configured to predict the likelihood of ovulation based on said data.

10. The system according to claim 1, further comprising a training unit configured to adjust the evaluation unit based on training data and/or individual user input.

11. The system according to claim 1, wherein the sensor is an optical heart rate sensor such as a photoplethysmography sensor.

12. The system according to claim 1, wherein the sensor is a body-worn sensor.

13. The system according to claim 1, wherein the sensor is detached from the subject, in particular a camera and/or a biofeedback device.

14. A method for unobtrusive fertility tracking, comprising the steps of:
- receiving a heart signal from a sensor;
- processing the heart signal; and
- analyzing the heart signal to predict likelihood of ovulation, wherein the method further comprises the steps of:
- extracting heart rate variability features from the heart signal; and
- predicting likelihood of ovulation by correlating absolute measures of the heart rate variability features to estrogen levels.

15. A non-transitory computer readable medium comprising a computer program comprising program code encoded on the computer readable medium, the program code for causing a processor to carry out the following steps:
- receiving a heart signal from a sensor;
- processing the heart signal;
- analyzing the heart signal to predict likelihood of ovulation, including:
  - extracting heart rate variability features from the heart signal; and
  - predicting likelihood of ovulation by correlating absolute measures of the heart rate variability features to estrogen levels.

16. The method according to claim 14, further comprising providing an activity indicator indicative of a current activity level and/or a user's physical condition, in particular a circadian rhythm or phase of the subject, the prediction based on said activity indicator.

17. The method according to claim 16, further comprising determining motion and/or orientation data of the subject, the activity indicator based on said motion and/or orientation data.

18. The method according to claim 16, further comprising determining an ambient temperature and/or ambient light levels, the activity indicator based on said ambient temperature and/or ambient light levels.

19. The method according to claim 16, further comprising tracking local date and time information, the activity indicator based on said local date and time information.

20. The method according to claim 14, further comprising integrating testing results from other fertility tracking devices, in particular luteinizing hormone testing devices and/or basal body temperature thermometers, the likelihood of ovulation predicted based on the heart signal and/or the testing results from other fertility tracking devices.

* * * * *